(12) United States Patent
Park (10) Patent No.: US 10,016,153 B2
(45) Date of Patent: Jul. 10, 2018

(54) PHOTOPLETHYSMOGRAPHIC MEASUREMENT METHOD AND APPARATUS

(71) Applicant: Samsung Electronics Co., Ltd., Suwon-si (KR)

(72) Inventor: Sang Yun Park, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 275 days.

(21) Appl. No.: 14/458,676

(22) Filed: Aug. 13, 2014

(65) Prior Publication Data

US 2015/0148633 A1 May 28, 2015

(30) Foreign Application Priority Data

Nov. 27, 2013 (KR) .................. 10-2013-0145051

(51) Int. Cl.
| | | |
|---|---|---|
| *A61B 5/1455* | (2006.01) | |
| *A61B 5/024* | (2006.01) | |
| *A61B 5/08* | (2006.01) | |
| *A61B 5/00* | (2006.01) | |

(52) U.S. Cl.
CPC ........ *A61B 5/14551* (2013.01); *A61B 5/0004* (2013.01); *A61B 5/02416* (2013.01); *A61B 5/0816* (2013.01); *A61B 5/6801* (2013.01)

(58) Field of Classification Search
CPC .............. A61B 5/1455; A61B 5/14551; A61B 5/14552; A61B 5/0205; A61B 5/0059; A61B 5/14532; A61B 5/6801; A61B 5/02416

USPC ....... 600/310, 322, 323, 324, 325, 339, 340, 600/341, 342, 473, 476; 356/41
See application file for complete search history.

(56) References Cited

U.S. PATENT DOCUMENTS

| | | | | |
|---|---|---|---|---|
| 3,638,640 A | * | 2/1972 | Shaw .................. | A61B 5/14552 356/41 |
| 4,213,052 A | * | 7/1980 | Caffarella ............... | H01J 65/08 250/462.1 |
| 5,584,296 A | * | 12/1996 | Cui .................... | A61B 5/14552 356/41 |

(Continued)

FOREIGN PATENT DOCUMENTS

| | | |
|---|---|---|
| JP | 3000010 U | 7/1994 |
| JP | 2005-52308 A | 8/2005 |

(Continued)

OTHER PUBLICATIONS

Lee, YongKwi, et al. "Development of a wristwatch-type PPG array sensor module." *2011 IEEE International Conference on Consumer Electronics—Berlin (ICCE-Berlin)*, Sep. 2011, 168-171.

*Primary Examiner* — Eric Winakur
*Assistant Examiner* — Chu Chuan (JJ) Liu
(74) *Attorney, Agent, or Firm* — NSIP Law (57) ABSTRACT

Provided are a photoplethysmographic measurement apparatus, a photoplethysmographic measurement method, and an apparatus for measuring a biosignal. The photoplethysmographic measurement apparatus includes a probe, a light emitter comprising a nonelectrical light source and disposed at one end of the probe, the light emitter configured to illuminate a measurement part, and a light receiver disposed at another end of the probe and configured to detect light reflected or transmitted by the illuminated measurement part.

18 Claims, 6 Drawing Sheets

(56) References Cited

U.S. PATENT DOCUMENTS

| | | | |
|---|---|---|---|
| 5,830,137 A * | 11/1998 | Scharf | A61B 5/14552 600/323 |
| 7,650,177 B2 * | 1/2010 | Hoarau | A61B 5/14552 600/323 |
| 7,869,849 B2 * | 1/2011 | Ollerdessen | A61B 5/14552 600/323 |
| 2004/0010299 A1 * | 1/2004 | Tolkoff | A61N 5/06 607/88 |
| 2004/0110111 A1 * | 6/2004 | Wasylucha | A61C 19/063 433/29 |
| 2007/0032721 A1 * | 2/2007 | Crane | A61B 5/0059 600/407 |
| 2007/0105176 A1 * | 5/2007 | Ibey | C12Q 1/54 435/14 |
| 2008/0298649 A1 | 12/2008 | Ennis et al. | |
| 2009/0234441 A1 | 9/2009 | Sweet et al. | |
| 2009/0326345 A1 * | 12/2009 | Jaffe | A61B 5/14553 600/323 |
| 2012/0197093 A1 | 8/2012 | LeBoeuf et al. | |
| 2013/0030259 A1 | 1/2013 | Thomsen et al. | |
| 2013/0043112 A1 * | 2/2013 | Rubio | H01H 23/146 200/331 |
| 2013/0060098 A1 | 3/2013 | Thomsen et al. | |
| 2013/0060109 A1 * | 3/2013 | Besko | A61B 5/14552 600/323 |

FOREIGN PATENT DOCUMENTS

| | | |
|---|---|---|
| JP | 2005-300587 A | 10/2005 |
| JP | 2009-302252 A | 12/2009 |
| JP | 2010-151877 A | 7/2010 |
| KR | 20-0390204 Y1 | 7/2005 |

\* cited by examiner

PHOTOPLETHYSMOGRAPHIC MEASUREMENT METHOD AND APPARATUS

CROSS-REFERENCE TO RELATED APPLICATION

This application claims the benefit under 35 USC 119(a) of Korean Patent Application No. 10-2013-0145051 filed on Nov. 27, 2013, in the Korean Intellectual Property Office, the entire disclosure of which is incorporated herein by reference for all purposes.

BACKGROUND

1. Field

The following description relates to a method and an apparatus of measuring a biosignal, a photoplethysmographic measurement apparatus and method, and a method of acquiring a photoplethysmogram (PPG).

2. Description of Related Art

With the widespread use of personalized electronic devices such as smartphones and tablet computers, various efforts have been directed to utilizing biosignals that are sequentially or continually measured from an individual in the fields of healthcare, personal well-being, entertainment and human-machine interface. A heart rate of a person may provide a variety of information about the health condition of the person, such as, for example, stress and exercise. A person's heartbeat may be relatively simply detected, and detecting two or more heartbeats may allow calculation of the heart rate. Likewise, a respiratory rate of a person provides a variety of information about the health condition of a person. Thus, a person's heart rate and respiratory rate are applied as preferred biosignals in various areas. A heart rate may be measured by many different methods. Photoplethysmography is a technique widely used along with electrocardiography in measuring the heart rate of a person. In contrast to electrocardiography, photoplethysmography may be applied to readily detect a heartbeat at terminal appendages, for example, a wrist, and a fingertip, and provide a photophlethysmogram (PPG) indicating the heart rate of a person. Photoplethysmography may refer to a method of exciting a light source beneath a layer of skin, measuring light reflected from a skin tissue or transmitted through a skin tissue, and generating a PPG of blood penetrating the skin tissue. Thus, a light source and a light receiving sensor may be considered the constituent elements of a device configured to generate a PPG In an example, an implementation of a light source may be omitted, and ambient light may be utilized. However, a signal may be greatly affected by changes in the ambient light; thus, use of the ambient light may be difficult in various environments. In a biosignal measuring environment in which a personalized electronic device and a wearable device are utilized, the weight and volume of a system may need to be minimized. Further, it is desirable to reduce the power consumption to provide a low-power system. Thus, among constituent elements to be used to implement a photoplethysmographic measurement, a device that may reduce the lack of reliability of ambient light while saving a driving power of the light source may be needed.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a photoplethysmographic measurement apparatus includes a probe, a light emitter comprising a nonelectrical light source and disposed at one end of the probe, the light emitter configured to illuminate a measurement part, and a light receiver disposed at another end of the probe and configured to detect light reflected or transmitted by the illuminated measurement part.

The nonelectrical light source may include at least one selected from the group consisting of a chemiluminescent light source, a bioluminescent light source, a phosphorescent light source, and a radioactive light source.

The chemiluminescent light source may include at least one selected from the group consisting of a luminol derivative, adamantane-dioxetane, an acridinium derivative, lucigenin, firefly luciferin, photoprotein, hydrazides, a Schiff base compound, an electrochemical luminescent substrate, and a luminescent oxygen channeling substrate.

The bioluminescent light source may include at least one selected from the group consisting of luciferase, horseradish peroxidase, alkaline phosphatase, β-galactosidase, and chloramphenicol acetyltransferase.

The nonelectrical light source may include the chemiluminescent light source or the bioluminescent light source, and the light emitter may be configured to be detachably attached to the apparatus.

The phosphorescent light source may include at least one selected from the group consisting of alkaline aluminate, silicate aluminate, strontium aluminate, europium aluminate, dysprosium aluminate, and calcium aluminate.

The radioactive light source may include tritium.

An intensity of the light emitted from the light source of the light emitter may range from 20 to 200 millicandelas per square meter ($mdc/m^2$).

A wavelength of the light emitted from the light source of the light emitter may range from 570 to 580 nanometers (nm).

The general aspect of the apparatus may further include an adhesive layer configured to be in contact with the measurement part.

The general aspect of the apparatus may further include a covering configured to block external light.

The general aspect of the apparatus may further include a transmitter configured to transmit a result obtained by the light receiver.

The general aspect of the apparatus may further include an oxygen saturation calculator configured to calculate an oxygen saturation level based on a result obtained by the light receiver.

A wavelength of the light emitted from the light emitter may range from 660 to 1,000 nm, and the apparatus may be configured to measure an intravascular oxygen saturation level.

In another general aspect, a method of using an apparatus including a nonelectrical light source and a light receiver is provided, the method involving illuminating a measurement part with the nonelectrical light source; detecting, with the light receiver, light reflected or transmitted by the illuminated measurement part; filtering a data signal from the light receiver; and calculating a photoplethysmogram of a user based on the filtered data signal.

The photoplethysmogram may provide information regarding a heart rate or a respiratory rate of the user.

In another general aspect, an apparatus for measuring a biosignal includes a nonelectrical light source configured to illuminate a measurement part, a light receiver configured to detect an electromagnetic radiation from the illuminated measurement part, and a processing unit configured to calculate light absorption by the illuminated measurement part based on the detected electromagnetic radiation.

The nonelectrical light source and the light receiver may be positioned on or within a probe.

The apparatus may be configured to be detachably attached to the measurement part of a user, and the apparatus may further include a transmitter configured to transmit a result obtained by the processing unit to a mobile terminal.

The probe may be configured to be attached to a mobile terminal, to connect to a mobile terminal via a port, or to wirelessly communicate with a mobile terminal.

Other features and aspects will be apparent from the following detailed description, the drawings, and the claims.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Herein, the term "connected to" or "coupled to" that is used to designate a connection or coupling of one element to another element includes both an instance in which an element is "directly connected or coupled to" another element and an instance in which an element is "electronically connected or coupled to" another element via still another element.

The term "on" that is used to designate a position of one element with respect to another element includes both an instance in which the one element is adjacent to the another element and an instance in which any other element exists between these two elements.

The term "comprises or includes" and/or "comprising or including" used in the document means that one or more other components, steps, operation and/or existence or addition of elements are not excluded in addition to the described components, steps, operation and/or elements unless context dictates otherwise.

Figure 1:
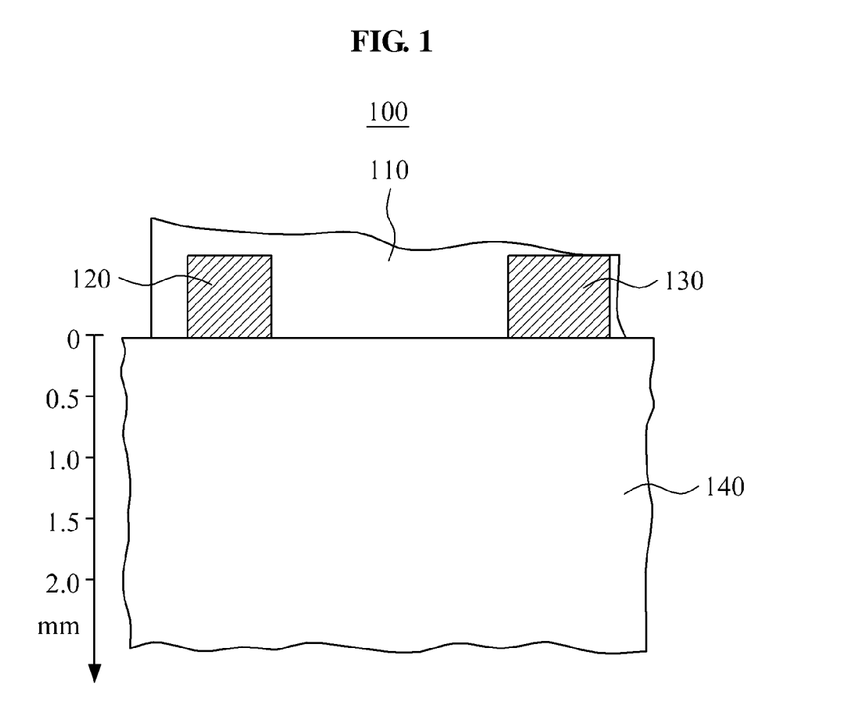
FIG. 1 is a cross-sectional view illustrating an example of a photoplethysmographic measurement apparatus.
Figure 2:
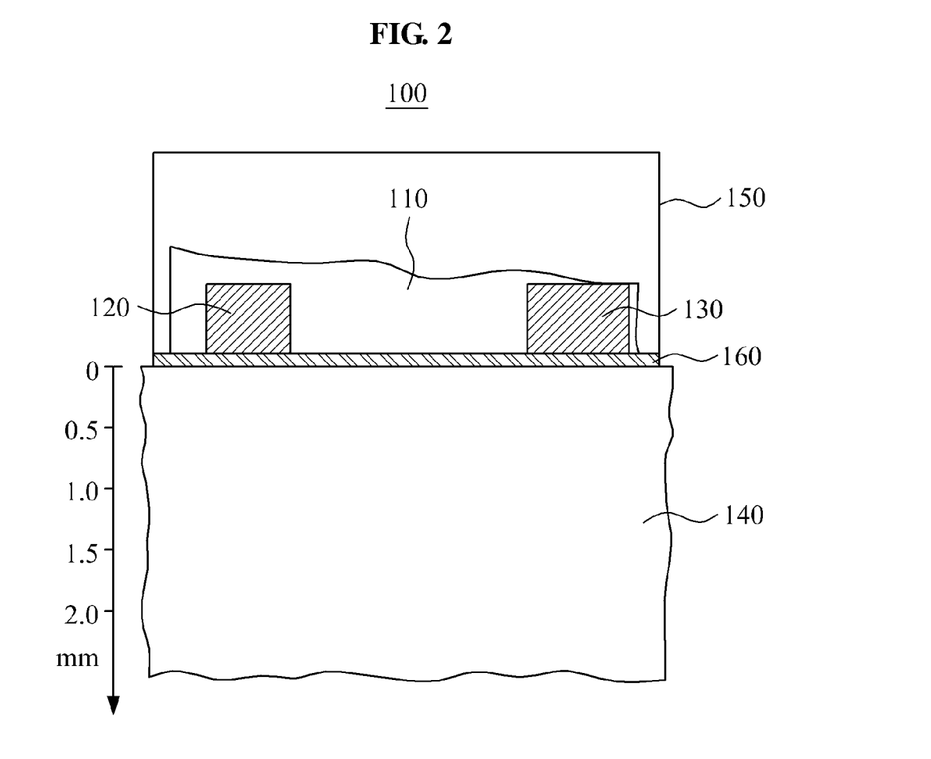
FIG. 2 is a cross-sectional view illustrating another example of a photoplethysmographic measurement apparatus.

FIG. 1 is a cross-sectional view illustrating an example of a photoplethysmographic measurement apparatus 100, and FIG. 2 is a cross-sectional view illustrating another example of a photoplethysmographic measurement apparatus 100.

Referring to FIG. 1, the photoplethysmographic measurement apparatus 100 includes a probe 110, a light emitter 120 disposed at one end of the probe 110, and a light receiver 130 disposed at another end of the probe 110. The probe 110 of the photoplethysmographic measurement apparatus 100 may be configured to be in contact with a measurement part 140 of a user. For example, the probe may directly contact the skin of the measuring part 140 of the user. The photoplethysmographic measurement apparatus 100 further includes a covering 150 configured to block external light, as shown in FIG. 2. For example, the covering 150 may be a case or a housing that surrounds the probe 110 and blocks external light from reaching the measurement part 140 of the user when the photoplethysmographic measurement apparatus 100 is detachably mounted on the user.

In this example, the term "light" refers to an electromagnetic radiation. An electromagnetic radiation that is outside the normal visual spectrum range of 390 to 700 nm may be applicable to the photoplethysmographic measurement. Thus, the term "light" may include an electromagnetic radiation having a wavelength of less than 390 nm or greater than 700 nm.

The photoplethysmographic measurement apparatus 100 may sense a change in a volume of blood flowing through a blood vessel of the measurement part 140 of the user using a nonelectrical light source, thereby measuring a PPG to be used to verify a state of activity of a heartbeat. The measurement part 140 of the user may include an ear, a finger, a toe, a neck, a wrist, and a forehead. The photoplethysmographic measurement apparatus 100 may further include an adhesive layer 160 to be in contact with the measurement part 140 of the user, as illustrated in FIG. 2. The adhesive layer 160 may have an opening near the light receiver 130. Alternately, the adhesive layer 160 may be made of a transparent material to allow the detection of light from the measurement part 140 while providing comfort to the user. The photoplethysmographic measurement apparatus 100 may be designed to attach to the skin of the user for an extended time, such as many hours or days, providing a continuous monitoring of the biosignals of the user. However, the present disclosure is not limited thereto.

The light emitter 120 may use the nonelectric light source that does not require a power source. The nonelectrical light source may include at least one of a chemiluminescent light source, a bioluminescent light source, a phosphorescent light source, and a radioactive light source. In an example in which a nonelectrical light source is used in the light emitter 120, it may be unnecessary to provide an additional power supply to drive the light source; thus, the power consumption of the device may be reduced and the size of the device may be minimized. In addition, the use of a nonelectrical light source may prevent the user from experiencing a thermal sensation or unpleasant sensation that may result from having an electrical light source on the skin, or even prevent a low-temperature burn that may be caused by the heat generated by such a light source.

The chemiluminescent light source may include at least one of a luminol derivative, adamantane-dioxetane, an acridinium derivative, lucigenin, firefly luciferin, photoprotein, hydrazides, a Schiff base compound, an electrochemical luminescent substrate, and a luminescent oxygen channeling substrate. Luminol may cause chemiluminescence of a 420-nanometer (nm) wavelength, and may undergo a chemiluminescent reaction by reacting with, for example, hydrogen peroxide.

The chemiluminescent light source may initiate a chemical reaction at a point in time desired by the user. Chemiluminescence may be maintained for a predetermined period of time based on an amount and a concentration of a chemical material being used. The chemiluminescent light source may lose a luminescence capability when the predetermined period of time elapses. Thus, in an example in which a chemiluminescent light source is used, the entire photoplethysmographic measurement apparatus may be implemented to be disposable, or a light emitter may be implemented to be detachable from the photoplethysmographic measurement apparatus for replacement.

For example, a luminol derivative may be used as a chemiluminescent light source material. In this example, when the luminol derivative is separated from hydrogen peroxide, a chemical reaction may not be initiated; thus, a non-luminescence state may be maintained until the light is necessary. An advantage of using a chemiluminescent light source is that it is possible to initiate a chemical reaction at a desired point in time while maintaining a non-luminescence state. By mixing the luminol derivative with hydrogen peroxide, a chemical reaction may be initiated, and light may be emitted as a result of the reaction. Luminescence may be strongest at an early stage of the reaction, and may be terminated when a chemical equilibrium is reached as the reaction progresses. An initial strength or a duration of the luminescence may be controlled by adjusting an amount, a concentration, and a mixing degree of a reactant. When the luminescence reaction reaches an equilibrium, a lifespan of the chemiluminescent light source material may expire. However, by inducing a reverse reaction, the chemiluminescent light source material may return to an initial separation state for reuse. When reuse by a reverse reaction is impossible, the photoplethysmographic photoplethysmographic measurement apparatus may be reused by replacing the light emitter.

The bioluminescent light source may include at least one of luciferase, horseradish peroxidase, alkaline phosphatase, β-galactosidase, and chloramphenicol acetyltransferase.

In an example in which a luciferase enzyme is used as a bioluminescent light source material, a biological reaction may not be initiated at a temperature lower than a body temperature; thus, a non-luminescence state may be maintained. When a bioluminescent light source is used, it is possible to initiate a biological reaction at a desired point in time while maintaining a non-luminescence state. In an example in which the photoplethysmographic measurement apparatus is worn on a human body, the luciferase enzyme may react based on temperature, a biological reaction may be initiated, and light may be emitted as a result of the reaction. Luminescence may be strongest at an early stage of the reaction, and may be terminated when a reaction equilibrium is reached as the reaction progresses. An initial strength or a duration of the luminescence may be controlled by adjusting an amount, a concentration, and a mixture state. When the luminescence reaction reaches an equilibrium, a lifespan of the bioluminescent light source material may expire. However, by inducing a reverse reaction, the bioluminescent light source material may return to an initial separation state for reuse. When reuse by a reverse reaction is impossible, the photoplethysmographic measurement apparatus may be reused by replacing the light emitter.

Similar to the chemiluminescent light source, the bioluminescent light source may initiate a biological reaction at a point in time desired by the user. Bioluminescence may be maintained for a predetermined period of time based on an amount and a concentration of a material being used. The bioluminescent light source may lose a luminescence capability when the predetermined period of time elapses. Thus, when a bioluminescent light source is used, the entire photoplethysmographic measurement apparatus may be implemented to be disposable, or a light emitter may be implemented to be detachable from the photoplethysmographic measurement apparatus for replacement.

The phosphorescent light source may include at least one of alkaline aluminate, silicate aluminate, strontium aluminate, europium aluminate, dysprosium aluminate, and calcium aluminate.

The phosphorescent light source may absorb ambient light and emit light for a predetermined period of time in a dark environment. When the phosphorescent light source is used, a light emitter may be exposed to ambient light for at least the predetermined period of time. Because a change in external light may affect the measurement taken by the light receiver, a covering or housing may be provided to block external light from the measurement part of the user. Although the light emitter exhausts a luminescence capability after the predetermined period of time elapses, the light emitter may reacquire the luminescence capability using external light accumulated through light re-absorption. Thus, the photoplethysmographic measurement apparatus may be reused, and an available time of the photoplethysmographic measurement apparatus may be extended on a semi-permanent basis.

The phosphorescent light source may be provided in a form of a pigment; thus, the light source may be easily applicable and provided in various colors. Accordingly, the photoplethysmographic measurement apparatus may measure a PPG by utilizing a light source having at least two wavelengths, and may apply the measured data to calculating oxygen saturation.

The radioactive light source may include tritium. Tritium may be relatively stable, and the light source may spontaneously emit light for years without a necessity of performing a separate light accumulation process, or initiating a chemical reaction or a biological reaction. Thus, an available time of the photoplethysmographic measurement apparatus may be extended semi-permanently.

An intensity of the light emitted from the light source of the light emitter 120 may range from 20 to 200 millicandelas per square meter ($mdc/m^2$).

A wavelength of the light emitted from the light source of the light emitter 120 may correspond to a green wavelength band ranging from 570 to 580 nm in the event of making a photoplethysmographic measurement of heart rate, and may correspond to a red wavelength of 660 nm to an infrared wavelength of 1,000 nm in the event of making an oxygen saturation measurement. In an example in which an electromagnetic radiation of an infrared wavelength band is used, a band greater than or equal to 1,000 nm may be utilized.

The light receiver 130 may sense light that is emitted from the light emitter 120 toward the measurement part 140, and reflected or transmitted.

The light receiver 130 may include an optical filter (not shown). The light receiver 130 may include at least one of a photo diode (PD), a charge-coupled device (CCD), and a complementary image sensor (CIS). The light receiver 130 may further include a light concentrator (not shown) configured to concentrate the reflected or transmitted light of the light emitter 120.

The photoplethysmographic measurement apparatus 100 may further include a pulsing apparatus (not shown) configured to pulse light emitted by the light emitter 120 by utilizing a liquid crystal matrix.

The photoplethysmographic measurement apparatus 100 may further include a transmitter configured to transmit a result obtained by the light receiver 130, and an oxygen saturation calculator configured to calculate an oxygen saturation level based on the result obtained from the light receiver 130. The photoplethysmographic measurement apparatus 100 may further include a power supply configured to supply power to the transmitter.

Figure 3:
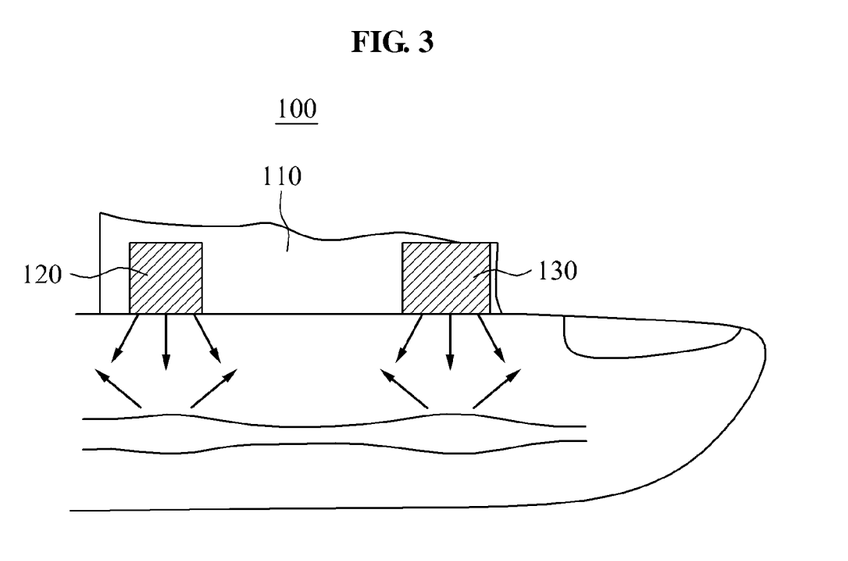
FIG. 3 is a view illustrating an example of wearing a photoplethysmographic measurement apparatus.
Figure 4:
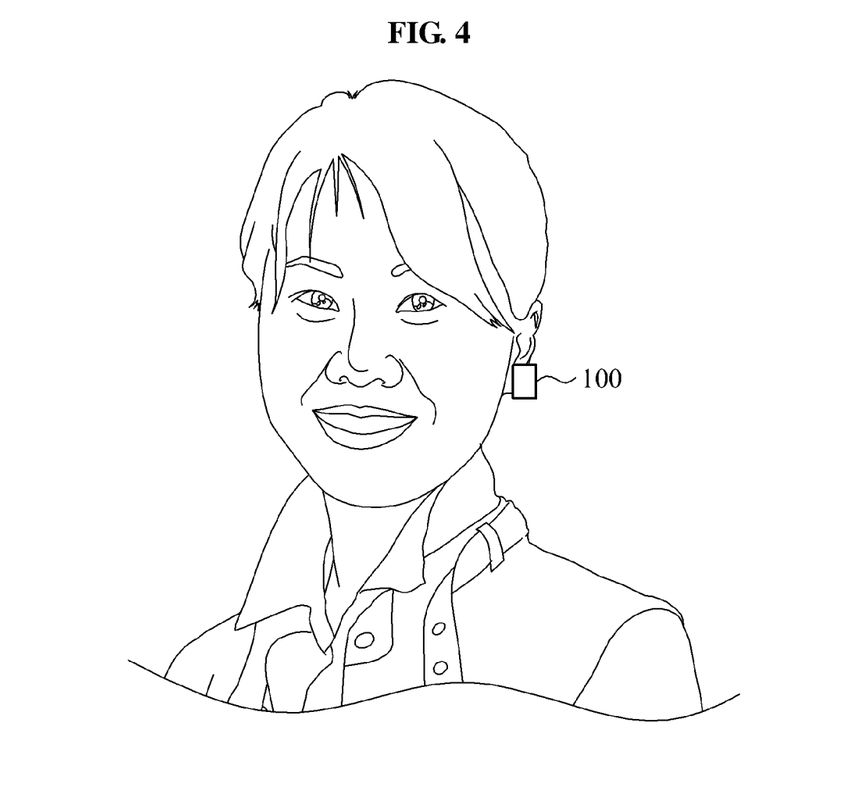
FIG. 4 is a view illustrating another example of wearing a photoplethysmographic measurement apparatus.

FIG. 3 is a view illustrating an example of wearing the photoplethysmographic measurement apparatus 100, and FIG. 4 is a view illustrating another example of wearing the photoplethysmographic measurement apparatus 100.

To measure a pulse or an oxygen saturation level of a user, the user may wear the photoplethysmographic measurement apparatus 100 on a finger as shown in FIG. 3, or may wear an earring-type photoplethysmographic measurement apparatus on an ear as shown in FIG. 4. Since a weight and a volume of the photoplethysmographic measurement apparatus 100 may be minimized, the user may conveniently wear the photoplethysmographic measurement apparatus 100.

Figure 5:
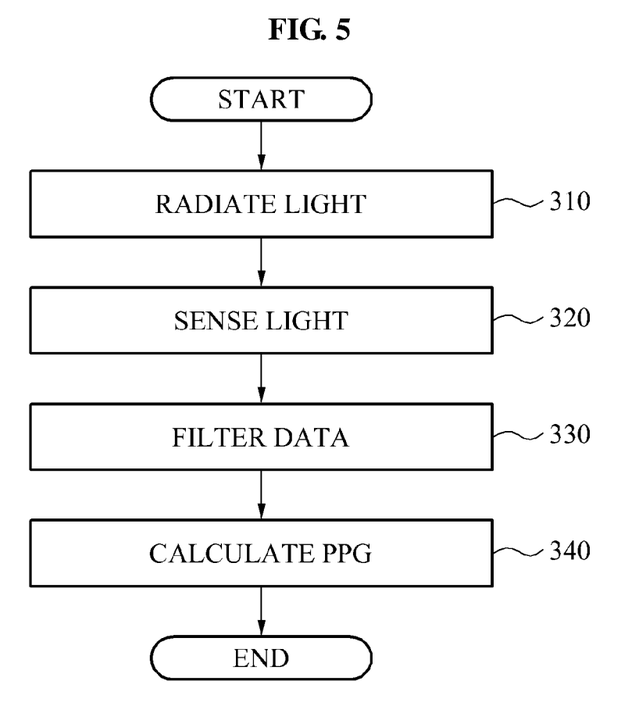
FIG. 5 is a flowchart illustrating an example of a photoplethysmographic measurement method.

FIG. 5 is a flowchart illustrating an example of a photoplethysmographic measurement method using a photoplethysmographic measurement apparatus.

The photoplethysmographic measurement method may be performed using the photoplethysmographic measurement apparatus including a probe, a light emitter including a nonelectrical light source, and a light receiver.

Referring to FIG. 5, the photoplethysmographic measurement method includes operation 310 of radiating light emitted from the nonelectrical light source of the light emitter toward a measurement part, operation 320 of sensing, by the light receiver, light that is emitted by the light source, and reflected or transmitted at the measurement part, operation 330 of amplifying and filtering a measured data signal sensed by the light receiver, and operation 340 of calculating a PPG of a user based on the filtered data signal.

In operation 310, light emitted from the nonelectrical light source of the light emitter is radiated toward the measurement part.

The nonelectrical light source may include, for example, at least one of a chemiluminescent light source, a bioluminescent light source, a phosphorescent light source, and a radioactive light source.

The measurement part of the user may include an ear, a finger, a toe, a neck, a wrist, and a forehead.

In operation 320, the light emitted from the light source, and reflected or transmitted at the measurement part is detected by the light receiver. The reflected or transmitted light sensed by the light receiver may be output in a form of an analog measurement signal from the light receiver.

In operation 330, the measured data signal detected by the light receiver is amplified and filtered. A digital measurement signal may be output by converting the analog signal to a digital signal, and data may be filtered using a filtering program, for example, algorithm. In this example, noise may be filtered out, and a significant PPG signal may be identified.

In operation 340, the PPG of the user is calculated based on the filtered data signal. The calculated PPG data may be provided through wired or wireless communication to the user, a medical institute including a doctor, a family or a friend of the user, a telecommunications company, an emergency medical treatment center, a person in charge at a local government, a health service provider providing a healthcare or insurance service, and/or a person or an organization related to health condition of the user.

Figure 6:
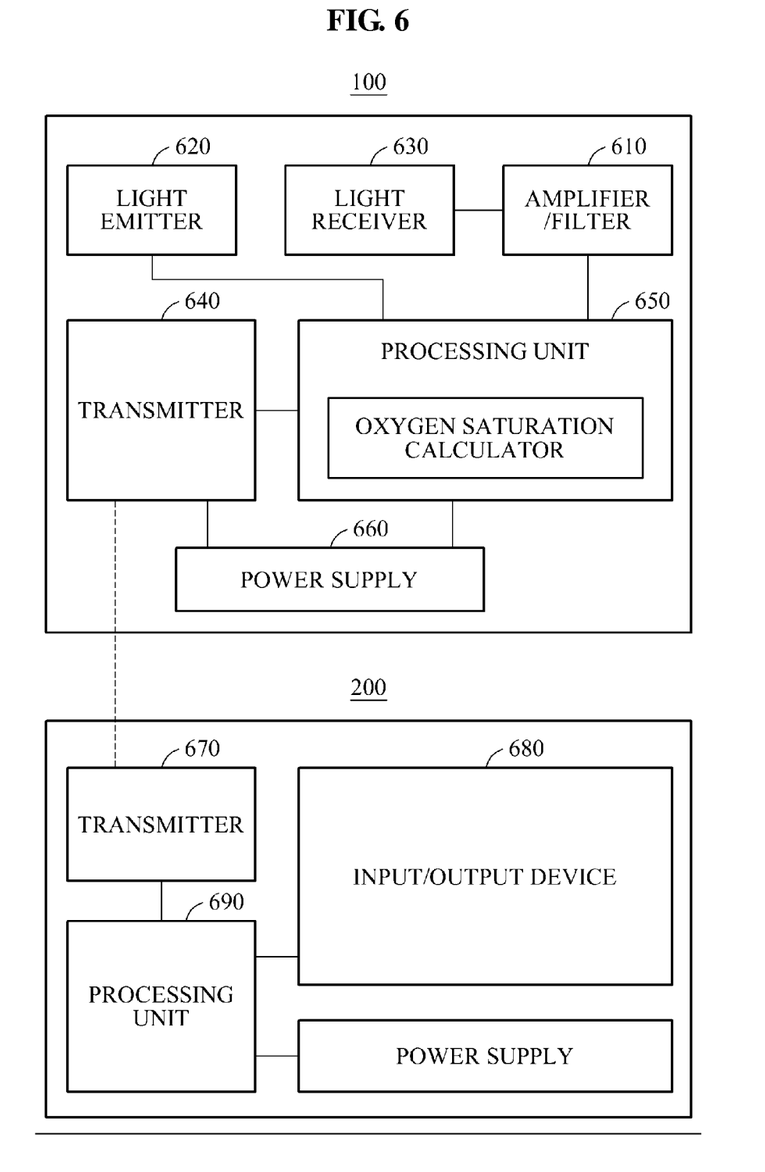
FIG. 6 is a schematic diagram illustrating an example of a photoplethysmographic measurement apparatus and a mobile terminal.

FIG. 6 illustrates a schematic diagram of another example of a photoplethysmographic measurement apparatus and an example of a mobile terminal configured to communicate with the photoplethysmographic measurement apparatus.

Referring to FIG. 6, the photoplethysmographic measurement apparatus 100 includes a light source 620, a light receiver 630, an amplifier/filter 610, a transmitter 640, a processing unit 650, and a power supply 660. However, the photoplethysmographic measurement apparatus of the present disclosure is not limited thereto; for instance, one or more elements may be absent or be located in a mobile terminal 200. The light emitter 620 may have the configuration of the light emitter 120 of FIG. 1. The light emitter 620 may be disposed at one end of a probe, and the light receiver 630 may be disposed at another end of the probe. In this example, a single probe includes both the light emitter 620 and the light receiver 630; however, in another example, more than one probe may be present or the light emitter 620 and the receiver 630 may be provided on separate probes. The photoplethysmographic measurement apparatus 100 may allow detachable attachment to a measurement part 140 of a user. For example, the apparatus 100 may have a shape of an earring, a ring, necklace or wrist band that may be worn continually for hours or days. In an example, the probe may contact the skin of the user. In another example, an adhesive layer may be disposed between the probe and the skin of the user. The description provided with respect to FIGS. 1-5 applies to the photoplethysmographic measurement apparatus 100 of FIG. 6; thus, repetitive descriptions are omitted for conciseness.

The light emitter 620 may include a nonelectric light source that does not require a power source, and may be configured to illuminate a measuring part of the user. The light receiver 630 may detect the light reflected or transmitted by the illuminated measuring part of the user. As a result, the light receiver 630 may obtain an analog signal relevant to determining the light absorbance by the skin of the user. The signal may be amplified and filtered by the amplifier/filter 610 to generate a digital signal that is sent to the processing unit 650.

Based on the signal received from the light receiver 630, the processing unit 650 determines the light absorbance of the skin over time, which may be used to generate a phtoplethysmogram and to determine a heart rate, a respiratory rate or other biosignals or physiological parameters of the user. The processing unit 650 may further include an oxygen saturation calculator configured to calculate an oxygen saturation level based on the data obtained from the light receiver 630. The transmitter 640 may transmit information regarding the biosignal of the user to a computing device such as a mobile terminal, a tablet computer, and the like. The power supply 660 may be configured to supply power to the transmitter 640 and the processing unit 650.

In this example, the transmitter 640 of the photoplethysmographic measurement apparatus 100 transmits the information regarding the biosignal to a mobile terminal 200, and the result may be displayed to the user via an input/output device 680 of the mobile terminal 200, such as a touch screen of the mobile terminal. The mobile terminal 200 may further transmit the information to other computing devices, a medical institute and the like; however, the present disclosure is not limited thereto. In another example, the probe may be attached to the mobile terminal 200, or the transmitter 640 may directly transmit the result of the processing unit 650 to a computing device or send the information to a medical institution or care providers.

A number of examples have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A mobile photoplethysmographic measurement wearable apparatus, comprising:
    a probe;
    a light emitter comprising a phosphorescent light source and disposed at one end of the probe, the light emitter configured to illuminate a measurement part in response to an environmental light-based stimulus external to the photoplethysmographic measurement wearable apparatus;
    a pulsing apparatus configured to pulse light emitted by the light emitter using a liquid crystal matrix;
    a light receiver disposed at another end of the probe and configured to measure light reflected or transmitted by the illuminated measurement part, and pulsed by the pulsing apparatus, in response to detection of the illumination of the measurement part;
    an oxygen saturation calculator configured to calculate an intravascular oxygen saturation level based on the result from the light receiver; and
    an adhesive layer in contact with the light emitter, the light receiver, and the probe,
    wherein the phosphorescent light source comprises at least one selected from the group consisting of alkaline aluminate, silicate aluminate, strontium aluminate, europium aluminate, dysprosium aluminate, and calcium aluminate, and
    wherein a wavelength of the light emitted from the light emitter ranges from 660 to 1,000 nm.

2. The apparatus of claim 1, wherein an intensity of the light emitted from the light source of the light emitter ranges from 20 to 200 millicandelas per square meter ($mdc/m^2$).

3. The apparatus of claim 1, wherein a wavelength of the light emitted from the light source of the light emitter ranges from 570 to 580 nanometers (nm).

4. The apparatus of claim 1, wherein the adhesive layer is configured to be in contact with the measurement part.

5. The apparatus of claim 1, further comprising a covering configured to block external light.

6. The apparatus of claim 1, further comprising a transmitter configured to transmit a result of the measuring by the light receiver.

7. The apparatus of claim 1, wherein the adhesive layer has a length exceeding a length of the probe.

8. The apparatus of claim 1, wherein the adhesive layer has a length equal to a length of a case disposed on the outside of the probe.

9. The apparatus of claim 1, further comprising an amplifier/filter configured to filter an analog signal from the light receiver in response to the signal being amplified.

10. The apparatus of claim 1, wherein the light receiver is directly connected to an amplifier/filter and directly adjacent to the light emitter, wherein the light receiver is disposed between the amplifier/filter and the light emitter.

11. A mobile photoplethysmographic measurement wearable apparatus, comprising:
    a probe;
    a light emitter comprising a chemiluminescent light source disposed at one end of the probe, the light emitter configured to illuminate a measurement part in response to an environmental heat-based stimulus external to the photoplethysmographic measurement wearable apparatus;
    a light receiver disposed at another end of the probe and configured to measure light reflected or transmitted by the illuminated measurement part in response to detection of the illumination of the measurement part, and
    an adhesive layer in contact with the light emitter and the light receiver,
    wherein the chemiluminescent light source comprises at least one selected from the group consisting of a luminol derivative, adamantane-dioxetane, an acridinium derivative, lucigenin, firefly luciferin, photoprotein, hydrazides, a Schiff base compound, an electrochemical luminescent substrate, and a luminescent oxygen channeling substrate,
    wherein a wavelength of the light emitted from the light emitter ranges from 660 to 1,000 nm, and the measuring by the light receiver includes measuring an intravascular oxygen saturation level, and wherein the chemiluminescent light source induces a reverse reaction to return to an initial separation state.

12. The apparatus of claim 11, wherein the light emitter is configured to be detachably attached to the apparatus.

13. A mobile photoplethysmographic measurement wearable apparatus, comprising:
    a probe;
    a light emitter comprising a radioactive light source configured to always provide illumination during the radioactive light source's luminous lifetime, and disposed at one end of the probe, the light emitter configured to continuously illuminate a measurement part;
a pulsing apparatus configured to pulse light emitted by the light emitter using a liquid crystal matrix;
a light receiver disposed at another end of the probe and configured to selectively measure detected light reflected or transmitted by the illuminated measurement part, and pulsed by the pulsing apparatus;
an oxygen saturation processor configured to calculate an oxygen saturation level based on a result of the measuring by the light receiver;
a transmitter configured to wirelessly transmit the calculated oxygen saturation level to a display device; and
an adhesive layer in contact with the light emitter and the light receiver.

14. The apparatus of claim 13, wherein the radioactive light source comprises tritium.

15. The apparatus of claim 13, wherein an intensity of the light emitted from the light source of the light emitter ranges from 20 to 200 millicandelas per square meter ($mdc/m^2$).

16. The apparatus of claim 13, wherein a wavelength of the light emitted from the light source of the light emitter ranges from 570 to 580 nanometers (nm).

17. The apparatus of claim 13, wherein the adhesive layer is configured to be in contact with the measurement part.

18. The apparatus of claim 13, wherein a wavelength of the light emitted from the light emitter ranges from 660 to 1,000 nm, and the measuring by the light receiver includes measuring an intravascular oxygen saturation level.

* * * * *